United States Patent [19]

Kilbride, Jr. et al.

[11] Patent Number: 5,236,920
[45] Date of Patent: Aug. 17, 1993

[54] GRANULATED RIBOFLAVIN PRODUCT HAVING HIGH FLOWABILITY, HIGH RIBOFLAVIN CONTENT

[75] Inventors: Terence K. Kilbride, Jr., Bloomfield Hills; Rudolph E. Lisa, Grosse Ile; Walter J. Tuman, Riverview, all of Mich.

[73] Assignee: Basf Corporation, Parsippany, N.J.

[21] Appl. No.: 947,083

[22] Filed: Sep. 18, 1992

Related U.S. Application Data

[63] Continuation of Ser. No. 845,795, Mar. 9, 1992, abandoned, which is a continuation of Ser. No. 516,416, Apr. 30, 1990.

[51] Int. Cl.⁵ ............................................. A23L 1/302
[52] U.S. Cl. ...................................... 514/251; 426/97; 426/274; 426/285; 426/294; 426/648
[58] Field of Search ...................... 426/72, 74, 97, 274, 426/285, 294, 648; 514/251

[56] References Cited

U.S. PATENT DOCUMENTS 4,486,435 12/1984 Schmidt et al. ...................... 514/241
4,868,180 9/1989 Izuhara et al. ....................... 514/241

*Primary Examiner*—Helen F. Pratt

[57] ABSTRACT

A free-flowing granulated riboflavin product has granules comprised of from about 75 to about 99.5 weight percent riboflavin. The riboflavin product exhibits a flowability index of from about 75 to about 750.

20 Claims, No Drawings

GRANULATED RIBOFLAVIN PRODUCT HAVING HIGH FLOWABILITY, HIGH RIBOFLAVIN CONTENT

This is a continuation of copending application Ser. No. 07/845,795, filed on Mar. 9, 1992, which is a continuation of Ser. No. 516,416 filed Apr. 30, 1990, both now abandoned.

BACKGROUND OF THE INVENTION

The present invention pertains to a granulated riboflavin product. Riboflavin in pure form exists as a clingy, dusty, highly electrostatic powder which sticks to and fouls processing equipment, and furthermore tends to bridge and clump during handling. These handling and processing problems have been overcome in the product of the present invention. The high flowability, of the product of the present invention can virtually eliminate product losses due to a buildup of riboflavin powder on processing equipment. Eliminating buildup of powder (i.e., fines) on the equipment also eliminates the labor which must be expended to remove the material from the equipment surfaces.

The granulated riboflavin product of the present invention has a heretofore unachieved combination of high vitamin B content (i.e., vitamin B content of at least 75 weight percent based on total product weight) together with high flowability (i.e., a flodex flowability index of at least 75).

The closest art known to the Inventors includes the following patents: U.S. Pat. No. 4,868,180; U.S. Pat. No. 3,962,384; U.S. Pat. No. 4,486,435; and European patent application 0,219,276. Although this art is the closest art of which the Inventors are aware, none of this art describes a product having the combined characteristics of: (1) high riboflavin content of the product of the present invention, together with (2) the high flowability of the product of the present invention. Furthermore, none of this art provides any quantified measurements which provide quantitative characterization of the level of flowability present in the products disclosed. Furthermore, only one of these patents (i.e., U.S. Pat. No. 4,868,180) refers to a "high" riboflavin product. As is shown by comparative examples herein, a product produced in accord with the method described in the '180 patent has a much lower flowability than that found in the product of the present invention. The product produced in the '180 patent is low in flowability because (1) the '180 patent describes a conventional fluid bed process, and (2) the '180 patent describes a process which requires pulverizing the agglomerated product in a Fitz mill using a punched screen. It has been found that the use of a Fitz mill results in the partial deagglomeration of the granules and hence the freeing up of individual crystals. It has been found that the fluid bed agglomeration process as described in the '180 patent fails to agglomerate at least 50 weight percent of the individual riboflavin crystals. Thus the product produced in the '180 patent comprises at least 50 weight percent pure riboflavin (i.e., riboflavin unassociated with any binder) due to both: (1) failure to granulate at least 50 weight percent of the vitamin in the fluid bed granulation step, as well as (2) the freeing up of individual riboflavin crystals in the milling step. Most importantly, however, it has been found that the product produced by the process described in the '180 patent has a flowability significantly lower than the flowability of the product of the present invention (see comparative Examples 7 and 8, infra).

None of the other art referred to above describes products which are "high" (i.e., greater than 75 weight percent) in riboflavin. Products having large amounts of binders (i.e., binder in an amount greater than 25 weight percent) permit the manufacture of products higher in flowability because the higher amount of binder provides a greater binding effect which in turn agglomerates more of the individual riboflavin crystals. Thus it is very difficult to make a product comprising 90 to 99 weight percent riboflavin with from 1 to 10 weight percent binder, because the relative proportion of binder is so small that it is very difficult to tie up (i.e., agglomerate) the individual crystals present. However, the product of the present invention comprises essentially no pure riboflavin. The Inventors of the product of the present invention have unexpectedly found that it is possible to agglomerate essentially all of the riboflavin in a product which has a surprisingly small amount of binder therein.

BRIEF SUMMARY OF THE INVENTION

The present invention pertains to a free-flowing granulated riboflavin product which comprises granules, wherein the granules are comprised of from about 75 weight percent to about 99.5 weight percent of riboflavin. The riboflavin product exhibits a flowability index (i.e., Flodex) of from about 75 to about 750.

It is an object of the present invention to provide a product which both (1) has a riboflavin content of at least 75 weight percent, as well as (2) exhibits a flowability of at least 75.

It is a further object of the present invention to provide a granulated riboflavin product having a riboflavin concentration high enough to render the product suitable for pharmaceutical end use.

It is a further object of the present invention to provide a granulated riboflavin product suitable for use in the manufacture of directly compressed tablets.

It is a further object of the present invention to provide a granulated riboflavin product which can be further processed without having substantial quantities adhere to the surfaces of the processing equipment.

It is a further object of the present invention to provide a food product which comprises a granulated riboflavin product.

DETAILED DESCRIPTION OF THE PREFERRED EMBODIMENTS

The present invention pertains to a riboflavin granulate. As used herein, the term granulate refers to solid particulates which are agglomerates of individual riboflavin crystals together with a relatively small amount of a binder. Generally, the granules are roughly spherical in shape, and have an average particle size of from about 50 microns to about 600 microns.

As stated above, the product of the present invention is predominantly comprised of riboflavin. Riboflavin is a crystalline solid 0.5 to 2 microns wide, and 1 to 25 microns long. Riboflavin has the undesirable qualities of static cling and dustiness, which together result in poor flowability. The agglomerated riboflavin granulate product of the present invention substantially eliminates these undesirable qualities, rendering the riboflavin suitable for further processing, especially suitable for direct compression into tablets. In general, the product of the present invention comprises riboflavin in an amount of from about 75 weight percent to about 99.5 weight percent. However, it is preferred that the riboflavin is present in an amount of from about 90 weight percent to about 99.5 weight percent, and it is most preferred that the riboflavin is present in an amount of from about 94 weight percent to about 96 weight percent.

A binder is also present in the product of the present invention. The binding agent may be a water-soluble binder, or a binder soluble in an organic solvent. The water-soluble binder may be a pregelatinized starch, water-soluble cellulose, a water-soluble high polymer, etc. A pregelatinized starch is a starch prepared by heating a dispersion of starch in water or a dry starch obtained by drying the same. The pregelatinized starch is exemplified by pregelatinized corn starches, pregelatinized potato starches, and pregelatinized modified starches [e.g., those described in Code of Federal Regulations (U.S.A.) §121, 1031a, b, c, d, e, f, g and h]. Furthermore there are pregelatinized dry commercial products such as Amycol C (Nichiden Chemical Company, Japan), Amylox (Nihon Corn Starch Company, Japan), Pre-Gel (Hublinder Company, U.S.A.), or Instant Cleargel (National Starch Company, U.S.A.).

Examples of water soluble celluloses include, for example, hydroxypropylcellulose, hydroxymethylcellulose, hydroxypropylmethylcellulose, carboxymethylcellulose, methylcellulose, etc. The water-soluble high molecular weight compounds (water-soluble high polymers) are exemplified by polyvinylpyrrolidone, polyvinyl alcohol, dextrin, gum arabic, gelatin, polydextrose, etc.

Binding agents soluble in organic solvents may be, for example, cellulose derivatives soluble in organic solvents, such as cellulose acetate phthalate, hydroxypropylmethylcellulose phthalate, ethylcellulose, etc. However, water-soluble binders (especially water-soluble celluloses) are preferred over binding agents soluble in organic solvents.

The solvent used to prepare a solution containing a binding agent for spraying includes water and organic solvents, for example lower alcohols (e.g., methylalcohol, ethylalcohol, isopropylalcohol, etc.) as well as ketones (e.g., acetone, etc.).

It is preferred that the binder utilized in the process is at least one water-soluble cellulose selected from the group consisting of hydroxypropylmethylcellulose, hydroxypropylcellulose, hydroxymethylcellulose, carboxymethylcellulose, and methylcellulose. It is most preferred that the binder is hydroxypropylmethylcellulose.

In general, the binder is present in the product in an amount of from about 0.5 weight percent to about 25 weight percent. Preferably, the binder is present in an amount of from about 0.5 weight percent to about 10 weight percent, and still more preferably the binder is present in an amount of from about 0.5 weight percent to about 6 weight percent. Most preferably, the binder is present in an amount of from about 3 weight percent to about 5 weight percent.

The granulated riboflavin product of the present invention may optionally contain a particulate absorbent material. The particulate absorbent material should be present as a coating on the outside of the granules. The absorbent is a material which improves the flowability of the granules and decreases any tendency of the granules to adhere to one another before the drying of the granules has been completed. Suitable particulate absorbents have been described in U.S. Pat. No. 4,486,435 and U.S. Pat. No. 3,962,384. The absorbents fall into two groups, with each of the above patents describing one of the groups. First, U.S. Pat. No. 3,962,384 describes an ultra-fine absorbent, which in general includes silicic acid, silicon dioxide or various silicates, along with other materials which may be equally effective due to physical properties as opposed to chemical composition. These absorbents are described as being insoluble in cold water, resistant to wetting by water, having an appreciable capacity to absorb and/or adsorb water and oil (i.e., an oil absorption capacity of from about 150 to 400 pounds per 100 pounds absorbent). Furthermore, they are free-flowing, they do not develop static electricity, and they have a particle size range of from about 2 microns to about 16 microns as well as a surface area of from about 175 to about 360 m$^2$/gm. Examples of these absorbents include silicic acid, silicas, alkali metal silicates, magnesium carbonate, kaolin clays, dicalcium phosphate, tricalcium phosphate and the like. A preferred absorbent from this group is silicic acid, a white amorphous powder, insoluble in water and having the empirical formula of $SiO_2 \cdot x H_2O$.

The second group of absorbents, i.e., those described in U.S. Pat. No. 4,486,435, are termed hydrophobic silica particles. Hydrophobic silicas are a special form of silica made from silica gel, precipitated silica or fumed silica, by a standard treatment known in the art. Such treatments involve the use of silanes or polysilanes to provide the desired hydrophobicity. It is also known to provide hydrophobic silicas by treatment of silica gel, precipitated silica or fumed silica with esterified coatings derived from high boiling alcohols. Other fine particle size materials characterized as hydrophobic may be as effective as the hydrophobic silicas since it is not so much the chemical composition of the final particle size coating composition which is critical, but rather the physical properties of the absorbent. Generally, the coating material must be substantially insoluble in water, have a primary particle size of from about 0.01 microns to about 0.04 microns, and have a surface area of from about 90 to about 130 m$^2$/gm. As can be seen in comparing the first group of silicas with the second group of silicas, the second group has a significantly smaller particle size as well as a special hydrophobic character, in comparison with the first group of absorbents. In the product of the present invention, it is most preferred to utilize an absorbent as described in the second group, i.e., as described in U.S. Pat. No. 4,486,435. However, in general, any of the absorbents from either group described above may be utilized in the product of the present invention. Preferably, however, the absorbent is a member selected from the group consisting of silicic acid, silica gel, an alkali metal silicate, magnesium carbonate, kaolin clay, dicalcium phosphate, and a hydrophobic silica having a primary particle size of from about 0.01 microns to about 0.04 microns and having a surface area of from about 90 to about 130 square meters per gram. Preferably, the absorbent is present in the product in an amount of from about 0.5 weight percent to about 5 weight percent. Preferably, the absorbent is present in amount of from about 0.5 weight percent to about 2 weight percent, and most preferably the absorbent is present at about 0.5 weight percent.

The granulated riboflavin product of the present invention is substantially dry. That is, the product of the present invention comprises water in an amount of from about 0.1 weight percent to about 4 weight percent. Preferably the product comprises water in an amount of from about 0.1 weight percent to about 0.75 weight percent, and most preferably the product comprises water in an amount of about 0.5 weight percent. It is desirable that the product have a low moisture content in order to both improve the flowability of the product and maintain a high riboflavin assay in the product.

The product of the present invention is substantially free of nonagglomerated riboflavin crystals. As used herein, the term nonagglomerated riboflavin crystals refers to solid particulates having a primary particle size of less than 25 microns. By being "substantially free of nonagglomerated riboflavin crystals it is meant that the product comprises less than 10 weight percent of such nonagglomerated riboflavin crystals. Since nonagglomerated riboflavin crystals are present only at very low levels in the product of the present invention, the invention exhibits significantly reduced dustiness and improved flowability over other riboflavin products. This low dustiness provides greater flowability as well as reduced adherence of the product to processing equipment. This in turn produces greater yield in downstream processing, as well as reduced fouling of equipment surfaces.

In general, the granulated riboflavin product of the present invention is comprised of granules having a geometric mean particle size of from about 50 microns to about 600 microns. Preferably, the geometric mean particle size is from about 50 microns to about 180 microns as well as from about 200 microns to about 600 microns. In the preferred size ranges, the 50–180 micron range is generally a granulated product produced via spray drying, whereas the 200 to 600 micron range is a granulated product produced via a rotary fluid bed granulation process. In general, the granules have a relatively high degree of size uniformity, i.e., the granules have a geometric mean particle size of from about 50 microns to about 600 microns, with a standard deviation of from about 0 to about 3. Preferably, if the granules have a geometric mean particle size of from about 200 microns to about 600 microns, the granules exhibit a standard size deviation of from about 1.5 to about 2.75. If the granules are produced via spray drying (i.e., have a geometric mean particle size of from about 50 microns to about 180 microns), the granules exhibit a standard deviation of particle size of from about 1.0 to 2.2).

The granulated vitamin B product of the present invention has excellent flowability. A high flowability means a high ability to flow along in a stream, i.e., as a fluid. The granulated vitamin B product of the present invention has a flowability as measured by the Flodex Method (described below) of from about 75 to about 750. The Flodex Method of determining flowability is described immediately below. Commonly, the flowability of the product is from about 100 to about 500, and most commonly the flowability is from about 150 to about 350. However, as a general rule, the highest flowability obtainable is the most desired flowability.

FLODEX METHOD FOR FLOWABILITY DETERMINATION

Flowability was measured using a Flodex ® Powder Flowability Index Test Instrument, Model 211, purchased from Hanson Research Corporation, 19727 Bahama Street, P.O. Box 35, Northridge, Calif., 91328. The Flodex ® apparatus presents a sample method for repeatable determination of powder flow characteristics. The Flodex ® device operates based upon the ability of a powder to fall freely through a hole in a plate. As used herein the Flowability Index was calculated by dividing 1000 by the orifice diameter in millimeters. For example, powder which will pass through an orifice diameter 4 millimeters in diameter, but not smaller, has a Flowability Index of 250.

The setup and operation of the Flodex ® Powder Flowability Index Test Instrument is thoroughly described in the Instruction Manual for the Flodex ® Model 211 apparatus, this Instruction Manual being hereby incorporated by reference. In addition, below is briefly described the method of determining flowability when using this device.

First, a 50 gram sample of the powder to be tested was used to fill the receptacle cylinder (funnel) to within about a centimeter from the top of the cylinder. The powder was carefully loaded onto the funnel so that there was no packing of the powder within the funnel, (of course, packing would have caused a loss of flowability of the powder). After the loading of the funnel, a minimum of 30 seconds was allowed to pass before the test was begun, in order to allow the possible formation of any flocculi. To begin the test, the release lever was slowly moved forward to drop open the hole closure, without vibration. If the test was positive, the open hole was visible from the top when looking down to see the hole at the bottom. The Flodex ® device should not be tapped or shaken during the test. If the test results were positive, the test was repeated with a smaller orifice diameter, until the orifice was of such a small diameter that a negative result (i.e., lack of flow) was achieved.

The Flodex ® apparatus is supplied with nineteen disks, from 4 to 32 millimeter hole diameters in one millimeter increments from 4 to 10 millimeters and in 2 millimeter increments for disks having a hole greater than 10 millimeters in diameter. In addition to these disks, the Inventors herein had 2 additional disks fabricated, one with a 2 millimeter hole, the other with a one millimeter hole. These two additional disks provided a means for determining flowability indexes of 500 and 1000, respectively.

In general, the granulated riboflavin product of the present invention should have a Flodex (i.e., flowability index) of from about 75 to about 750, and preferably the Flodex is from about 100 to about 500. Most preferably, the Flodex is from about 150 to about 350.

The granulated riboflavin product of the present invention can be produced in a variety of methods. However, the examples below illustrate two general methods by which the product can be produced: (1) spray drying and (2) rotary fluid bed granulation. It has been surprisingly found that either of these processes can be utilized to produce a high riboflavin content granulate which has a very low level of nonagglomerated riboflavin crystals therein. Furthermore, both of these processes have been found to produce granules having a geometric mean particle size of between 50 microns and 600 microns, with standard deviations of from 0-3.

EXAMPLE 1

This example illustrates the preparation of a free-flowing, spray-dried substantially static-free riboflavin powder containing over 75% by weight riboflavin in the spray-dried powder.

In a five gallon tank containing 66.18 parts of water were heated to 40° C. by a hot plate. 1.61 Parts of water-soluble hydroxypropylmethylcellulose (sold under the trade name "Methocel E-5") were then dissolved into the hot water, with stirring. Thereafter, 32.21 parts by weight of a commercially available riboflavin powder having a purity of 99% to 100% were then added to the solution of water and hydroxypropylmethylcellulose, to yield a yellow/orange suspension of riboflavin. This slurry was then homogenized by a Gifford-Wood homogenizer(manufactured by Greerco). The homogenization was continued for approximately 15 minutes, resulting in the reduction of the viscosity to about 385 centipoise.

Utilizing a laboratory size spray drying apparatus, having a variable speed atomizing wheel, feed tanks, and pump, the previously prepared homogenized riboflavin suspension was metered to the atomizing wheel. The atomizing wheel (a slotted-wheel obtained from Niro Atomizers, Inc., 9165 Rumsey Rd., Columbia, Md., as used in utility dryer Model IV) was operated at 21,000 rpms, a centrifugal speed of about 8,000 meters per minute. The inlet air temperature flowing into the spray dryer chamber was about 200° C., and the outlet air temperature was about 100° C. The riboflavin suspension was fed into the spray atomizing wheel at a rate of about 125 grams per minute.

The resulting granulated riboflavin product was an orange, free-flowing, static-free powder having a bulk density of 0.43 grams per cubic centimeter with a geometric mean particle size of about 58 microns and a log standard deviation of about 1.5 microns. Furthermore, the product had a flowability index, as measured by the Flodex method of at least 333. A flowability index greater than 100 is indicative of excellent flowability. The product mixed well in flour premixes and produced directly compressible tablets with the hardness of 12 scu. The final product (i.e., upon completion of drying) was made up of about 94 weight percent riboflavin, 5 weight percent binder, and 1 weight percent water.

EXAMPLE 2

In a five gallon tank, 72 parts of water were heated to 40° C., and 1.45 parts of water-soluble hydroxypropylmethylcellulose (sold under the trade name "Methocel E-5"), were dissolved into the hot water, with stirring. Thereafter, 26.55 parts by weight of a commercially available riboflavin powder having a purity of 99% to 100% were added to the solution to yield a yellow/orange suspension of riboflavin. This suspension was then homogenized by a Gifford-Wood homogenizer (manufactured by Greerco). The homogenization was carried out for approximately 15 minutes in order to reduce the viscosity. The final viscosity of the suspension was about 200 centipoise. The now homogenized riboflavin suspension was metered into the atomizing wheel of a laboratory size spray-drying apparatus, the apparatus having a variable speed atomizing wheel, feed tanks, and pump. The atomizing wheel was operated at 35,000 rpm, with a centrifugal speed of about 5,600 meters per minute. The spray drying apparatus had an inlet temperature of about 200° C. and an outlet temperature of about 120° C.

The resulting spray-dried, granulated riboflavin product exhibited poor flowability, and contained a great deal of static cling, and had a bulk density of 0.23 grams per cubic centimeter. The geometric mean particle size of this powder was about 41 microns, with a log standard deviation of about 1.5 microns. The flowability index, as measured by the Flodex method, was found to be about 50, i.e., indicative of poor flowability. The low flowability is an indication that this powder will perform poorly in tableting and flour premix tests. The low flowability and bulk density present in the product produced in this example is believed to be due to the small geometric mean particle size. The product was made up of about 94.5 weight percent riboflavin, 5.0 weight percent binder, and 0.5 weight percent water.

EXAMPLE 3

In a 750 gallon tank, 1.68 parts of water-soluble hydroxypropylmethylcellulose, sold under the trade name "Methocel E-5" were added to 66.45 parts of water, with the hydroxypropylmethylcellulose being dissolved into the hot water, with stirring. Thereafter, 33.55 parts (by weight) of a commercially available riboflavin powder having a purity of 99% to 100% were added to the mixture to yield a yellow/orange suspension of riboflavin. This suspension was then homogenized by a Gifford-Wood Homogenizer by Greerco. After homogenization was finished, the suspension had a viscosity of about 350 centipoise.

The riboflavin suspension was then metered into the atomizing wheel within a commercial spray dryer, the spray dryer having a variable speed atomizing wheel, feed tanks, and pump. The variable speed atomizing wheel was operated at about 8,000 rpm, a centrifugal speed of about 5,110 meters per minute. The spray dryer had an inlet air temperature of about 232° C. and an outlet air temperature of about 90° C.

The resulting granulated riboflavin product was a free-flowing, static-free powder having a bulk density of 0.37 grams per cubic centimeter with a geometric mean particle size of about 172 microns and a log standard deviation of about 1.5 microns. The flowability index, as measured by the Flodex method, was found to be equal to or greater than 333. This product mixed well in flour premixes and produced directly compressible tablets with a hardness of 12.0 scu. The product was made up of about 94.6 weight percent riboflavin, 5 weight percent binder, and 0.4 weight percent water.

EXAMPLE 4

This example illustrates the positive effective produced by hydrophobic silica on the flowability of the product.

A riboflavin slurry was prepared and sprayed using the conditions outlined in Example 3, except that a silica cloud was maintained within the spray-dryer by screw feeding a hydrophobic synthetic silica, sold under the trademark "Aerosil R-972", so as to provide a coating on the spray-dried droplets. This silica coating ultimately constituted between 1 and 2 weight percent of the total weight of the resulting spray-dried riboflavin powder.

The resulting riboflavin powder was very similar in particle size distribution and bulk density to the powder produced by Example 3. The powder was free-flowing, static-free, and had a bulk density of 0.37 grams per cubic centimeter with a geometric mean particle size of about 170 microns, with a log standard deviation of about 1.0 microns. The difference between the product of Example 4 and the product of Example 3 was the flowability index. The powder produced with 1% hydrophobic silica had a flowability index of about 500, which was significantly greater than the flowability value measured for the powder produced in Example 3. The product produced according to Example 4 mixed well in flour premixes and produced direct compression tablets with a hardness of 15.5 scu. The product was made up of about 94.6 weight percent riboflavin, 4.0 weight percent binder, 0.4 weight percent water, and 1 weight percent absorbent (i.e., hydrophobic silica).

EXAMPLE 5

This example illustrates a rotary fluid bed process for the preparation of a free-flowing, granulated, static-free riboflavin product which contained over 75% by weight riboflavin in the granulated product, which also contained about 0.5% moisture.

The binder solution was formulated in a five-gallon tank containing 92 parts of water, heated to 40° C. by a hot plate. 8 Parts of water-soluble hydroxypropyl methylcellulose, sold under the trademark "Methocel E-5", were dissolved into the hot water by stirring. This mixture was stirred for approximately 0.5 hours to completely dissolve the Methocel E-5.

3 Kilograms of a commercially available riboflavin powder having a purity of 99% to 100% were charged into the bowl of a laboratory size roto-granulator, having a variable speed rotating disc (which had a diameter of about 480 millimeters), feed tanks, and binder solution pump. The riboflavin was fluidized by two distinct forces: the rotating disk, turning at 200 rpm, and fluidizing air, with between 200 and 300 cubic feet per minute being passed through the slit (a gap of about 2 millimeters) between the rotating disk the wall of the fluid bed. After the riboflavin was fluidized, the previously prepared binder solution was sprayed tangentially, at a rate of 165 grams per minute, into the riboflavin cloud through a two fluid 1.2 mm nozzle utilizing 3.0 bar air to atomize the binder solution. After the binder addition was complete, the granulated riboflavin product was dried by raising the inlet temperature of the fluidizing air to 72° C.

The resulting riboflavin product was an orange, free-flowing, static-free powder having a bulk density of 0.48 grams per cubic centimeter and a geometric mean particle size of about 250 microns with a log standard deviation of 1.94 microns. The flowability index, as measured by the Flodex method, was found to be about 200. Any value greater than or equal to 100 is indicative of excellent flowability. The product was made up to about 96 weight percent riboflavin, 3.75 weight percent binder, and 0.25 weight percent water. The resulting granulate was directly compressed to form tablets. The tablets had a harness of 15.5 scu.

EXAMPLE 6

This example illustrates the necessity of homogenizing the riboflavin, binder and water slurry if a spray-dried granulate is being produced.

In a five-gallon tank containing 66.18 parts of water heated to 40° C. by a hot plate, and 1.61 parts of water-soluble hydroxypropyl methylcellulose (sold under the trade name "Methocel E-5") were dissolved into the hot water by stirring with a "Lightnin" brand mixer with a 3.5 inch marine prop blade. Thereafter, 32.21 parts by weight of a commercially available riboflavin powder, having a purity of 99% to 100%, were added to the mixture, while stirring with the Lightnin mixer, to yield a yellow/orange suspension of riboflavin. The slurry had the consistency of a paste, and its viscosity was in excess of 8,000 centipoise. In this form the slurry was not suitable for spray drying because this paste could not be pumped or, more importantly, atomized using conventional spray drying equipment.

The slurry was then homogenized, using a Gifford-Wood homogenizer, for approximately 15 minutes. This reduced the viscosity to 385 centipoise. This slurry was then spray dried under the conditions present in Example 1. The resulting spray-dried granulate was the same as the granulate described in Example 1.

EXAMPLE 7

This example illustrates that a fluid bed was not suitable for granulating riboflavin because a fluid bed did not completely fluidize the riboflavin crystals. This phenomenon prevented the production of a homogeneous granulated product in a fluid bed.

While 95 parts of riboflavin crystals and 1 part silica, Aerosil 200, a fluidizing aid, were being fluidized in a fluidized bed granulator (a Glatt CPCG 5-UD manufactured by Glatt AG of West Germany, using dry air heated up to 60° C.), an 8 weight percent aqueous solution containing hydroxypropylmethylcellulose was sprayed onto the fluidized powders up to the amount equivalent to 4 parts on a dry basis. The spraying of the binder solution was conducted over an 8.5 minute time period. Fluidization continued for an additional 28 minutes to completely dry the powder.

The product had the following particle size distribution:

| Sieve Designation A.S.T.M. -E-11-61 | Sieve Opening Microns | Weight % Retained On |
|---|---|---|
| 6 | 3,360 | 13 |
| 20 | 841 | 35 |
| 40 | 420 | 31 |
| 60 | 250 | 16 |
| 100 | 149 | 4 |
| 120 | 125 | 1 |
| Pan | — | 0 |

The bulk density of the resulting product was 0.30 grams per cubic centimeter and the powder contained 0.25 weight percent water. The particles larger than 841 microns were spherical and possessed no mechanical strength. Upon handling they would break apart into a fine yellow powder. This powder was ungranulated riboflavin crystals (i.e., agglomerated riboflavin) and the large balls were formed by electrostatic forces generated by fluidizing the ungranulated riboflavin crystals during the drying step. In contrast, the remaining powder (i.e., that fraction which passed through a 20 mesh sieve), consisted of orange granulated particles and possessed a flowability index (as measured by the Flowdex method) of 71. The product produced in the fluid bed was not suitable for tableting. The large spherical balls significantly reduced the flowability. This prevented an even distribution and steady flow of riboflavin through the die of the tablet press. However, of the granulated particles, those particles which passed through a 20 mesh sieve were suitable, and produced directly compressible tablets with a hardness of 25 scu.

The lack of mechanical strength of the large spherical particles, i.e., particles larger than 841 microns, combined with the exceptionally hard tablets produced from the granulated material, i.e., particles smaller than 841 microns, indicated that the product was not homogeneous, i.e., approximately 50% of the powder was ungranulated riboflavin crystals while the other 50% was granulated. However, because the amount of binder sprayed into the fluidized riboflavin was designed to produce an agglomerated powder with a 95% assay, on a dry basis, and 50% of the powder was ungranulated, the assay of the granulated material was much lower than was desired. Analytical analysis confirmed that the particles greater than 841 microns were ungranulated and that they possessed a riboflavin assay of 100%, while the granulated particles had a riboflavin assay of 89.1%.

In spite of the fact that the above-described Example did not result in the production of a riboflavin granulate having a flowability of from 75 to 750, the inventor is aware that certain fluid bed processes can in fact, occasionally produce such a granulate. However, in order to produce such a riboflavin granulate with a fluid bed, the inventors have discovered that (1) the rate of addition of binder solution must be lower than is commercially desired; (2) the process is only operable on larger-than-lab-scale fluid beds; (3) chopper blades may be required; (4) drying times are longer than commercially desired.

EXAMPLE 8

This example illustrates that Fitz milling the powder produced in a fluid bed granulator (which was performed in example 7 of the U.S. Pat. No. 4,868,180) does not improve the flowability or suitability for use in direct compressible tablets or food blends.

While 95 parts of riboflavin crystals were fluidized in a fluidized bed granulator using dry air heated to 50° C., a 5 weight % aqueous solution containing hydroxypropyl methylcellulose was sprayed onto the fluidized powders up to the amount equivalent to 3 parts on a dry basis. Fluidization continued for an additional 15 minutes to completely dry the powder. The powder was pulverized in a Fitz mill using a punched screen with openings 1.5 mm in diameter. The resulting powder was dusty, static prone, and exhibited flow in large clumps. It had a flowability index of 33, by the Flowdex method, and a bulk density of 0.26 grams per cubic centimeter.

The embodiments of the invention in which an exclusive privileged or property is claimed are defined as follows:

1. A free-flowing granulated riboflavin product which comprises granules of riboflavin in an amount of from about 75 weight percent to about 99.5 weight percent, said riboflavin product exhibiting a flowability index of from about 75 to about 750.

2. A free-flowing granulated riboflavin product as described in claim 1, wherein the product has a flowability of from about 100 to about 500.

3. A free-flowing granulated riboflavin product as described in claim 1, wherein the product has a flowability index of from about 150 to about 350.

4. A free-flowing granulated riboflavin product as described in claim 1 wherein the product further comprises a binder in an amount of from about 25 weight percent to about 0.5 weight percent, and wherein the binder is at least one member selected from the group consisting of pregelatinized starches, water-soluble celluloses, and water-soluble, edible, high polymers, said edible, high polymers being selected from the group consisting of polyvinylpyrrolidone, polyvinyl alcohol, dextrin, gum arabic, gelatin and polydextrose.

5. A granulated riboflavin product as described in claim 4 wherein the binder is present in an amount of from about 0.5 weight percent to about 10 weight percent.

6. A free-flowing granulated riboflavin product as described in claim 4 wherein the binder is present in an amount of from about 3 to about 5 weight percent.

7. A free-flowing granulated riboflavin product as described in claim 1 wherein the granulate has a flowability index of from about 100 to about 500 and wherein the granulate further comprises a binder in an amount of from about 0.5 weight percent to about 25 weight percent, and wherein the binder is at least one member selected from the group consisting of pregelatinized starches, water-soluble celluloses, and water-soluble, edible high polymers, said edible high polymers being selected from the group consisting of polyvinylpyrrolidone, polyvinyl alcohol, dextrin, gum arabic, gelatin and polydextrose.

8. A free-flowing granulated riboflavin product as described in claim 7 wherein the binder is at least one water-soluble cellulose selected from the group consisting of hydroxypropylcellulose, hydroxyethylcellulose, hydroxypropylmethylcellulose, carboxymethylcellulose and methylcellulose.

9. A free-flowing granulated riboflavin product as described in claim 7 wherein the granulate comprises at least one pregelatinized starch selected from the group consisting of pregelatinized corn starches, pregelatinized potato starches, and pregelatinized modified starches.

10. A free-flowing granulated riboflavin product as described in claim 1 wherein granules within the product have a geometric mean particle size of from about 50 microns to about 600 microns.

11. A free-flowing granulated riboflavin product as described in claim 10 wherein the granules have a geometric mean particle size of from about 50 microns to about 600 microns with a standard deviation of from about 0 to about 3.

12. A free-flowing granulated riboflavin product as described in claim 10 wherein the granulates have a geometric mean particle size of from about 200 microns to about 600 microns with a standard deviation of from about 1.5 to about 2.75.

13. A free-flowing granulated riboflavin product as described in claim 10 wherein the granulates have a geometric mean particle size of from about 50 microns to about 100 microns with a standard deviation of from about 1.0 to about 2.2.

14. A free-flowing granulated riboflavin product as described in claim 1 wherein the granules further comprise water in an amount of from about 0.1 weight percent to about 4 weight percent.

15. A free-flowing granulated riboflavin product as described in claim 4 wherein the granulate has a flowability index of from about 100 to about 500, and wherein the granulate further comprises water in an amount of from about 0.1 weight percent to about 0.75 weight percent.

16. A free-flowing granulated riboflavin product as described in claim 8 wherein the riboflavin is present in an amount of at least 90 weight percent, and wherein the binder is present in an amount of from about 0.5 weight percent to about 6 weight percent, and wherein water is present in an amount of from 0.1 weight percent to about 0.5 weight percent.

17. A free-flowing granulated riboflavin product as described in claim 1 wherein the product further comprises an absorbent in an amount of from about 0.5 weight percent to about 5 weight percent, wherein the absorbent is at least one member selected from the group consisting of hydrophobic silica, silicic acid, silica gel, an alkali metal siliate, magnesium carbonate, kaolin clay, and dicalcium phosphate.

18. A free-flowing granulated riboflavin product as described in claim 17 wherein the product further comprises an absorbent in an amount of from about 0.5 weight percent to about 2 weight percent, the absorbent being a hydrophobic silica having a primary particle size of from about 0.01 microns to about 0.04 microns.

19. A free flowing granulated riboflavin product as described in claim 17 wherein the product comprises riboflavin in an amount of from about 94 weight percent to about 96 weight percent, binder in an amount of from about 3 weight percent to about 5 weight percent, water in an amount of about 0.5 weight percent and silica in an amount of about 0.5 weight percent.

20. A free-flowing riboflavin product as described in claim 1, wherein said granules have a riboflavin content of at least about 90 weight percent.

* * * * *